(12) United States Patent
Tillman et al.

(10) Patent No.: US 6,884,931 B2
(45) Date of Patent: Apr. 26, 2005

(54) RICE HYBRID RH101

(75) Inventors: Barry L. Tillman, Friendswood, TX (US); Eugenio S. Sarreal, Pearland, TX (US)

(73) Assignee: RiceTec, Inc., Alvin, TX (US)

( * ) Notice: Subject to any disclaimer, the term of this patent is extended or adjusted under 35 U.S.C. 154(b) by 190 days.

(21) Appl. No.: 10/233,006

(22) Filed: Aug. 30, 2002

(65) Prior Publication Data

US 2004/0045059 A1 Mar. 4, 2004

(51) Int. Cl.[7] .......................... A61H 5/00; A61H 5/10; A61H 1/00; A61H 1/02; C12N 5/04
(52) U.S. Cl. .................. 800/320.2; 800/260; 800/265; 800/269; 435/421; 435/430; 435/430.1
(58) Field of Search .................. 800/260, 265, 800/269, 320.2, 274, 277–278, 300, 302, 303; 435/421, 430, 430.1

(56) References Cited

U.S. PATENT DOCUMENTS 5,523,520 A * 6/1996 Hunsperger et al. ........ 800/260

OTHER PUBLICATIONS

Kraft et al. Theoretical and Applied Genetics. 101: 323–326 (2000).*
Eshed and Zamir. Genetics. 143: 1807–1817 (1996).*
Yu et al. Proc. Natl. Acad. Sci. 94: 9226–9231 (1997).*
C.N. Bollich, B.D. Webb, M.A. Marchetti and J.E. Scott Registration of 'Lemont' Rice Sep./Oct. 1985 pp. 883–885.
Bennetzen, Jeffrey L., et al., 1992, Approaches and Progress in the Molecular Cloning of Plant Disease Resistance Genes, Genetic Engineering, vol. 14, pp. 99–124.
DeBolle, Miguel F.C., et al., 1996, Antimicrobial Peptides from *Mirabillis jalapa* and *Amaranthus caudatus*: Expression, Processing, Localization and Biological Activity in Transgenic Tobacco, Plant Molecular Biology, vol. 31, pp. 993–1008.
Eshed, et al., 1996, Less–Than–Additive Epistatic Interactions of Quantitative Trait Loci in Tomato, Genetics, vol. 143, pp. 1807–1817.
Kraft, et al., 2000, Linkage Disequilibrium and Fingerprinting.in Sugar Beet, Theoretical Applied Genetics, vol. 101, pp. 323–326.
Pang, Sheng–Zhi, et al., 1992, Expression of a Gene Encoding a Scorpion Insectotoxin Peptide in Yeast, Bacteria and Plants, Gene, vol. 116, pp. 165–172.

* cited by examiner

*Primary Examiner*—David T. Fox
*Assistant Examiner*—Keith O. Robinson
(74) *Attorney, Agent, or Firm*—Jondle & Associates P.C.

(57) ABSTRACT

A novel rice hybrid, designated RH101, is disclosed. The invention relates to the seeds of rice hybrid RH101, to the plants of rice RH101 and to methods for producing a rice plant produced by crossing the parent known as P1015 with the sterile line designated as S0505. The invention further relates to hybrid rice seeds and plants produced by crossing the hybrid RH101 with another rice cultivar.

9 Claims, No Drawings

RICE HYBRID RH101

BACKGROUND OF THE INVENTION

The present invention relates to a new and distinctive rice hybrid, designated RH101. Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 to 16 cm deep is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U.S. long-grain hybrids cook dry and fluffy when steamed or boiled, whereas medium- and short-grain hybrids cook moist and sticky. Long-grain cultivars have been traditionally grown in the southern states and generally receive higher market prices.

Rice plants (*Oryza sativa*) naturally self-pollinate and have perfect flowers, that are they have both male and female structures within the same flower. Rice plants, left to themselves, will self-pollinate and will therefore be substantially homozygous at most gene loci.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to low temperatures, and better agronomic characteristics on grain quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars and hybrids; those still deficient in a few traits may be used as parents to produce new populations for further selection.

These processes, which lead to the final step of marketing and distribution, usually take from eight to 12 years from the time the first cross is made and may rely on the development of improved breeding lines as precursors. Therefore, development of new cultivars and hybrids is a time-consuming process that requires precise forward planning, efficient use of resources, and a minimum of changes in direction.

Once a single plant is homozygous at all or nearly all loci, a rice variety can be produced from this single plant through simple generational advance, as long as external pollen flow is controlled and any apparent off-types in the population are removed. Developing sterile and pollinator lines for rice hybrids requires additional steps beyond developing varieties. The hybridizing system used in this invention is referred to as the 2-line system, because only 2 parental lines are required.

The development of hybrid parents, while a part of the selection process from the initiation of the breeding cross, nonetheless requires more steps, and more time. Not only do the lines have to be developed and purified (as described above), but then hybrid seed must be produced, and all possible hybrid combinations must be tested to find the best combination.

In developing hybrid rice lines, it is essential to utilize parent lines which, when combined, will give optimal quality and yield characteristics. Also, both parents must have seed production performance which will result in an economically viable hybrid. Most importantly, rice hybrids must fit farmers' production systems without requiring extensive operational changes.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard hybrid. If a single observation is inconclusive, replicated observations provide a better estimate of its genetic worth.

The goal of plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars and hybrids which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice parents or hybrids.

The development of new rice parent lines involves the selection of parental lines which collectively contain all required genotypic traits. Crosses (one or several) will be required, and the progeny from these crosses will be the starting point for further development.

Pedigree breeding and recurrent selection breeding methods are used to develop parent lines from breeding populations. Breeding programs combine desirable traits from two or more cultivars or various broad-based sources into breeding pools from which parent lines are developed by selfing and selection of desired phenotypes. The new parent lines are used to produce experimental hybrids, which are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines, hybrids or mixtures of phenotypically similar lines are tested for potential release as new parent lines or hybrids.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987).

Proper testing should detect any major faults and establish the level of superiority or improvement over current cultivars and hybrids. In addition to showing superior performance, there must be a demand for a new cultivar or hybrid that is compatible with industry standards or which creates a new market. The introduction of a new hybrid will incur additional costs to the seed producer, the grower, processor and consumer; for special advertising and marketing, altered seed and commercial production practices, and new product utilization. The testing preceding release of a new hybrid should take into consideration research and development costs as well as technical superiority of the final hybrid. For seed-propagated hybrids, it must be feasible to produce seed easily and economically.

Rice, Oryza sativa L., is an important and valuable field crop. Thus, a continuing goal of plant breeders is to develop stable, high yielding rice cultivars and hybrids that are agronomically sound. The reasons for this goal are obviously to maximize the amount of grain produced on the land used and to supply food for both animals and humans. To accomplish this goal, the rice breeder must select and develop rice plants that have the traits that result in superior cultivars and hybrids.

SUMMARY OF THE INVENTION

According to the invention, there is provided a novel rice hybrid, designated RH101. This invention thus relates to the seeds of rice hybrid RH101, to the plants of rice hybrid RH101 and to methods for producing a rice hybrid by crossing the parent lines of rice hybrid RH101.

The invention also relates to methods of producing hybrid rice plants by crossing inbred rice line P1015 as a pollen donor, with male-sterile rice S-Lines to restore fertility in the $F_1$ hybrid plants. Further, the invention relates to hybrid rice plants and seeds in which inbred rice line S0505 is the female parent.

Thus, any such methods using the rice variety RH101 are part of this invention: selfing, backcrosses, hybrid production, crosses to populations, and the like. All plants produced using rice variety RH101 as a parent are within the scope of this invention.

In another aspect, the present invention provides for hybrid RH101 where either parent or both parents are single gene converted parent lines of RH101. The single transferred gene may preferably be a dominant or recessive allele. Preferably, the single transferred gene will confer such traits as herbicide resistance, insect resistance, resistance for bacterial, fungal, or viral disease, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of rice plant RH101. Preferably, the regenerable cells in such tissue cultures will be embryos, protoplasts, meristematic cells, callus, pollen, leaves, anthers, root tips, flowers, seeds, panicles or stems. Still further, the present invention provides rice plants regenerated from the tissue cultures of the invention.

DEFINITIONS

In the description and tables which follow, a number of terms are used. In order to provide a clear and consistent understanding of the specification and claims, including the scope to be given such terms, the following definitions are provided:

Days to 50% heading. Average number of days from seeding to the day when 50% of all panicles are exerted at least partially through the leaf sheath. A measure of maturity.

Grain Yield. Grain yield is measured in pounds per acre and at 14.0% moisture. Grain yield of rice is determined by the number of panicles per unit area, the number of fertile florets per panicle, and grain weight per floret.

Lodging Percent. Lodging is measured as a subjective rating and is percentage of the plant stems leaning or fallen completely to the ground before harvest.

Grain Length (L). Length of a rice grain is measured in millimeters.

Grain Width (W). Width of a rice grain is measured in millimeters.

Length/Width (L/W) Ratio. This ratio is determined by dividing the average length (L) by the average width (W).

1000 Grain Wt. The weight of 1000 rice grains as measured in grams.

Harvest Moisture. The percent of moisture of the grain when harvested.

Plant Height. Plant height in centimeters is taken from soil surface to the tip of the extended panicle at harvest.

Total Milling. Total milled rice as a percent of rough rice.

Protein. Percent of protein in the milled grain.

Breakdown. The peak viscosity minus the hot paste viscosity.

Apparent Amylose Percent. The most important grain characteristic that describes cooking behavior in each grain class, or type, i.e., long, medium and short grain. The percentage of the endosperm starch of milled rice that is amylose. Standard long grains contain 20 to 23% amylose. Rexmont type long grains contain 24 to 25% amylose. Short and medium grains contain 16 to 19% amylose. Waxy rice contains 0% amylose. Amylose values will vary over environments.

S0505: Line Pei Ai 64s_

P1015: Line Lemont

Alkali Spreading Value. Indicator of gelatinization temperature and an index that measures the extent of disintegration of milled rice kernel in contact with dilute alkali solution. Standard long grains have 3 to 5 Alkali Spreading Value (intermediate gelatinization temperature).

RVA Viscosity. Rapid Visco Analyzer is a new and widely used laboratory instrument to examine paste viscosity, or thickening ability of milled rice during the cooking process.

Hot Paste Viscosity. Viscosity measure of rice flour/water slurry after being heated to 95 Centigrade. Lower values indicate softer and stickier cooking types of rice.

Paste Temperature (also called Initial viscosity increase temperature). The temperature at which a defined flour-water mixture exhibits a measurable viscosity increase under a standardized, instrument-specific (Rapid Visco Analyser) cooking cycle.

Paste Time. The time at which a defined flour-water mixture exhibits a measurable viscosity increase under a standardized, instrument-specific (Rapid Visco Analyser) cooking cycle.

Final Viscosity. Viscosity achieved at the end of a Rapid Visco Analyser cooking cycle.

Peak Time. The time at which peak (maximum) hot-paste viscosity is attained during a standardized, instrument-specific (Rapid Visco Analyser) cooking cycle.

Trough (also called hot-paste viscosity). The viscosity of a defined flour-water mixture after it has been heated to, and held, at the maximum temperature of a standardized, instrument-specific (Rapid Visco Analyser) cooking cycle.

Trough time. The time at which the Trough (hot-paste viscosity) occurs when a defined flour-water mixture has been heated to and held at the maximum temperature of a standardized, instrument-specific (Rapid Visco Analyser) cooking cycle.

Amylose percent (also called apparent amylose). A linear fraction of starch that is correlated with cooking and eating qualities. The apparent amylose content of milled rice may be classified as waxy (less than 2%), low (7–20%), intermediate (20–25%) and high (over 25%). Apparent amylose is normally determined on breeding selections. It is based on iodine colorimetry at pH 4.5–4.7.

Alkali Spreading Value (ASV). Number from 1 to 7 indicating the susceptibility of intact milled rice kernels to alkali disintegration. A low value is given to rice that does not readily digest in alkali. The test is typically used in breeding to screen gelatinization temperature of rice.

Starch Index. The sum of apparent amylose value plus alkali spreading value. This value correlates with cooking properties of rice.

Chalk. An opaque region of the rice kernel due to loose packing of the starch granules. Chalk may occur throughout or in a part of the kernel.

Whole Milling (also called Head rice milling yield). The quantity of milled head (¾-whole) rice produced in the milling of rough rice to a well-milled degree, usually expressed in the United States as percent of rough rice by weight.

Total Milling (also called Milling yield). The quantity of total milled rice produced in the milling of rough rice to a well-milled degree; it is usually expressed as percent of rough rice by weight, but when specified, may be expressed as percent of brown rice.

Cold Paste Viscosity. Viscosity measure of rice flour/water slurry after being heated to 95° C. and uniformly cooled to 50° C. (American Association of Cereal Chemist). Values less than 200 for cold paste indicate softer cooking types of rice.

Consistency. Cold paste viscosity minus hot paste viscosity.

Gelatinization temperature. The temperature at which a defined flour-water mixture exhibits a measurable viscosity increase under a standardized, instrument-specific, cooking cycle (also known as "initial viscosity increase temperature").

Peak temperature, at peak viscosity. The temperature at which peak hot paste viscosity is attained.

Peak viscosity, hot paste. The maximum viscosity attained during heating when a standardized, instrument-specific protocol is applied to a defined rice flour and water slurry.

Setback viscosity. Cold paste viscosity minus peak hot paste viscosity.

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents (recurrent parent), for example, a first generation hybrid $F_1$ with one of the parental genotypes of the $F_1$ hybrid.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Single Gene Converted. Single gene converted or conversion plant refers to plants which are developed by a plant breeding technique called backcrossing wherein essentially all of the desired morphological and physiological characteristics of an inbred are recovered in addition to the single gene transferred into the variety via the backcrossing technique or via genetic engineering.

Relative Maturity. Days to 50% heading relative to a common check variety such as Cypress.

DETAILED DESCRIPTION OF THE INVENTION

The present invention relates to a hybrid rice, designated, and seeds and plants derived from the hybrid. The invention also relates to hybrid plants and seeds and any further progeny or descendants of the hybrid derived by crossing RH101 as a pollen donor. The invention is also directed to methods for producing a rice plant by crossing a first parent rice plant with a second parent rice plant wherein the first parent rice plant is P1015 and the second parent rice plant is S0505. Rice plant from the RH101 hybrid. Thus, any methods using the hybrid rice line RH101 in backcrosses, hybrid production, crosses to populations, and the like, are part of this invention. All plants which are a progeny of or descend from hybrid rice line RH101 are within the scope of this invention.

Rice hybrid RH101 is a high yielding, very early maturing, photoperiod insensitive, long grain male fertile hybrid rice line. It is produced from the cross of the male fertile line P1015, and the male sterile line S0505. It has been tested against the common varietal checks Cocodrie, Wells and Cypress in more than 80 replicated trials. The hybrid has shown uniformity and stability, as described in the following hybrid description information. It has been produced and tested a sufficient number of generations with careful attention to uniformity of plant type. The hybrid has been increased with continued observation for uniformity of the parent lines.

Rice Hybrid RH101 has the following morphologic and other characteristics (based primarily on data collected at Alvin, Tex.).

Variety Description Information

MATURITY

Days to maturity: 107 days from planting to harvesting

Maturity Class (50% heading—South): Very Early (70–85 days)

CULM (Degrees from perpendicular after flowering)

Angle: Erect (less than 30)

Length: 120 cm (Soil level to top of extended panicle on main stem)

Height Class: tall

Internode Color (After flowering): Green

Strength (Lodging resistance): Moderately Strong

FLAG LEAF (After Flowering)

Length: 37 cm

Width: 2.1 cm

Pubescence: Pubescent

Leaf Angle (After flowering): horizontal

Blade Color: Green

Basal Leaf Sheath Color: Green

LIGULE

Color (Late vegetative state): White

Shape: 2-Cleft

Collar Color (Late vegetative stage): Pale green

Auricle Color (Late vegetative stage): Pale green

PANICLE

Length: 27 cm

Type: Intermediate

Secondary Branching: Light
Exsertion (near maturity): 90–99% exserted
Axis: Droopy
Shattering: Moderate (1–5%)
Threshability: Easy
GRAIN
Awns (After full heading): Absent
Apiculus Color (At maturity): purple apex
Stigma Color: Purple
Stigma exsertion (At flowering): >50%
Lemma and Palea Color (At maturity): Straw
Lemma and Palea Pubescence: pubescent
Spikelet Sterility (At maturity): Highly fertile (>90%)
GRAIN (Seed)
Seed Coat Color: Light brown
Endosperm Type: Nonglutinous (non-waxy)
Endosperm Translucency: Intermediate
Endosperm Chalkiness: Small (less than 10% of sample)
Scent: Nonscented
Shape Class: Long Measurements:

| | Length (mm) | Width (mm) | L/W Ratio | 1000 Grains (grams) |
|---|---|---|---|---|
| Milled | 6.86 | 2.16 | 3.18 | 19.0 |

Milling Yield (% whole kernel (head) rice to rough rice): 46–54%
Amylose: 23%
Alkali Spreading value: 3.3 (1.5% KOH Solution)
Gelatinization temperature type: High
RESISTANCE TO LOW TEMPERATURE
Germination and Seedling Vigor:
Flowering (Spikelet fertility):
SEEDLING VIGOR NOT RELATED TO LOW TEMPERATURE
Vigor:
BLAST RESISTANCE (*Pyricularia oryzae*)
Group/Number: IB-1, 5, 45, 49, 54; IC-1, 17; ID-1, 13; IE-1; IG-1; IH-1.
RESISTANCE TO OTHER DISEASES
Sheath Blight *Rhiuzoctonia solani*: 7 (check=Gulfmont=7)
Straight Head: 3, (check: Cypress=2; Gulfmont=2)
Kernel Smut *Neovossia horrida/Tilletia barclayana*: 7 (check=Cypress=7)

Hybrid designated RH101 has shown uniformity and stability within the limits of environmental influence for all the traits as described above. The parents have been self pollinated a sufficient number of generations with careful attention paid to uniformity of plant type to ensure homozygosity and phenotypic stability. The parental lines have been increased both by hand and in isolated fields with continued observation for uniformity. No variant traits have been observed or are expected in RH101.

This invention is also directed to methods for producing a rice plant by crossing a first parent rice plant with a second parent rice plant, wherein the first or second rice plant is the rice plant from the hybrid RH101. Further, both first and second parent rice plants may be from the hybrid RH101. Therefore, any methods using the hybrid RH101 are part of this invention: selfing, backcrosses, hybrid breeding, and crosses to populations. Any plants produced using hybrid RH101 as a parent are within the scope of this invention.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, leaves, stems, anthers and the like. Thus, another aspect of this invention is to provide for cells which upon growth and differentiation produce a hybrid having essentially all of the physiological and morphological characteristics of RH101.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation, in Methods in Plant Molecular Biology & Biotechnology" in Glich, et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in Methods in Plant Molecular Biology & Biotechnology, Glich, et al., (Eds. pp. 67–88 CRC Press, 1993); and by Phillips, et al., "Cell-Tissue Culture and In-Vitro Manipulation" in Corn & Corn Improvement, 3rd Edition; Sprague, et al., (Eds. pp. 345–387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of *Agrobacterium* vectors systems and methods for *Agrobacterium*-mediated gene transfer provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using the microprojectile media delivery with the biolistic device *Agrobacterium*-medicated transformation. Transformant plants obtained with the protoplasm of the invention are intended to be within the scope of this invention.

The present invention contemplates a rice plant regenerated from a tissue culture of a variety (e.g., RH101) or hybrid plant of the present invention. As is well known in the art, tissue culture of rice can be used for the in vitro regeneration of a rice plant. Tissue culture of various tissues of rices and regeneration of plants therefrom is well known and widely published. For example, reference may be had to Chu, Q. R., et al., (1999) "Use of bridging parents with high anther culturability to improve plant regeneration and breeding value in rice", Rice Biotechnology Quarterly 38:25–26; Chu, Q. R., et al., (1998), "A novel plant regeneration medium for rice anther culture of Southern U.S. crosses", Rice Biotechnology Quarterly 35:15–16; Chu, Q. R., et al., (1997), "A novel basal medium for embryogenic callus induction of Southern US crosses", Rice Biotechnology Quarterly 32:19–20; and Oono, K., "Broadening the Genetic Variability By Tissue Culture Methods", Jap. J. Breed. 33 (Suppl.2), 306–307, illus. 1983, the disclosures of which are hereby incorporated herein in their entirety by reference. Thus, another aspect of this invention is to provide cells which upon growth and differentiation produce rice plants having the physiological and morphological characteristics of variety RH101.

Tables

The following tables present data on the Yield performance of the hybrid RH101 as compared to Cypress. The traits and characteristics of rice hybrid plants and grain resulting the hybrid RH101 are compared with Cypress, a commonly grown rice variety in the U.S. The data was collected from multiple locations and repeated trials.

The results in Table 1 compare yield, plant height, maturity, lodging and milling yields of Cypress versus the hybrid of the present invention produced by crossing P1015 with S0505. As shown in Table 1 of the present invention, the hybrid RH101 unexpectedly has significantly higher yield than Cypress, is significantly taller than Cypress, and has significantly lower total milling and whole milling yields. The following symbols may be shown in the table. "*" indicates significance at 1%; "" indicates significance at 5%, "*" indicates significance at 10% and "ns" indicates nonsignificant.

Further Embodiments of the Invention

This invention also is directed to methods for producing a rice plant by crossing a first parent rice plant with a second parent rice plant wherein either the first or second parent rice plant is a hybrid rice plant RH101. Further, both first and second parent rice plants can come from the hybrid rice RH101. Still further, this invention also is directed to methods for producing a hybrid rice line RH101-derived rice plant by crossing hybrid rice line RH101 with a second rice plant and growing the progeny seed, and repeating the crossing and growing steps with the hybrid rice line RH101-derived plant from 0 to 7 times. Thus, any such methods using the hybrid rice line RH101 are part of this invention: selfing, backcrosses, hybrid production, crosses to populations, and the like. All plants produced using hybrid rice line RH101 as a parent are within the scope of this invention, including plants derived from hybrid rice line RH101.

It should be understood that the parents of hybrid RH101 can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, kernels, ears, cobs, leaves, husks, stalks, roots, root tips, anthers, silk and the like.

Duncan, et al., *Planta* 165:322–332 (1985) reflects that 97% of the plants cultured that produced callus were capable

TABLE 1

|  | Yield kg/ha | Plant Ht. cm | Days to Heading | Lodging % | Total Milling % | Whole Milling % |
| --- | --- | --- | --- | --- | --- | --- |
| Cypress | 7243.2 | 93.8 | 84.2 | 0.4 | 0.6862 | 0.6197 |
| RH101 | 8806.5 | 112.3 | 76.3 | 18.8 | 0.6836 | 0.5202 |
| Obs rvations | 110 | 106 | 114 | 110 | 94 | 94 |
| Difference | −1563.3 | −18.5 | 7.9 | −18.4 | 0.0026 | 0.0995 |
| Probability | <.0001*** | <.0001*** | <.0001*** | <.0001*** | $0.6217^{ns}$ | <.0001*** |

The results of Table 2 compare the basic quality characteristics of RH101 and Cypress. Unexpectedly, RH101 had significantly higher amylose, lower ASV and starch index than Cypress. Also, the grain length and width and chalk are significantly greater than Cypress, and the L/W is significantly lower.

TABLE 2

|  | Amylose % | ASV | Starch Index | Length mm | Width Mm | L/W ratio | Chalk % |
| --- | --- | --- | --- | --- | --- | --- | --- |
| Cypress | 21.9 | 4.39 | 27.1 | 6.63 | 2.08 | 3.18 | 2.47 |
| RH101 | 23.4 | 3.8 | 26.3 | 6.74 | 2.18 | 3.08 | 5 |
| Obs rvations | 39 | 46 | 39 | 46 | 46 | 46 | 46 |
| Difference | −1.5 | 0.59 | 0.8 | −0.11 | −0.1 | 0.1 | −2.53 |
| Probability | <.0001*** | 0.0053*** | 0.0295** | 0.0201** | <.0001*** | 0.0002*** | 0.0954* |

Starch characters are compared in Table 3. Peak, trough, trough time and breakdown are not different between Cypress and RH101. RH101 has a lower peak time, paste time, final viscosity, setback and consistency, and higher past temperature.

TABLE 3

|  | Peak | Peak Tim | Trough | Trough Time | Paste Temp | Paste Tim | Fianal Visc | Breakdown | Setback | Consistency |
| --- | --- | --- | --- | --- | --- | --- | --- | --- | --- | --- |
| Cypress | 351.50 | 9.04 | 127.20 | 13.30 | 74.30 | 5.30 | 263.90 | 224.30 | −87.60 | 136.70 |
| RH101 | 352.30 | 8.93 | 130.10 | 13.20 | 74.90 | 5.50 | 290.30 | 222.20 | −62.00 | 160.20 |
| Observations | 10 | 10 | 10 | 10 | 10 | 10 | 10 | 10 | 10 | 10 |
| Difference | −0.80 | −0.11 | −2.90 | 0.10 | −0.60 | −0.20 | −26.40 | 2.10 | −25.60 | −23.50 |
| Probability | $0.8688^{ns}$ | 0.0846* | $0.6171^{ns}$ | $0.1429^{ns}$ | 0.012 | 0.0115 | 0.0505* | $0.6592^{ns}$ | 0.0182 | 0.0193 | of plant regeneration. Subsequent experiments with both inbreds and hybrids produced 91% regenerable callus that produced plants. In a further study in 1988, Songstad, et al., *Plant Cell Reports* 7:262–265 (1988), reports several media additions that enhance regenerability of callus of two inbred lines. Other published reports also indicated that "nontraditional" tissues are capable of producing somatic embryogenesis and plant regeneration. K. P. Rao et al., *Maize Genetics Cooperation Newsletter,* 60:64–65 (1986), refers to somatic embryogenesis from glume callus cultures and B. V. Conger, et al., *Plant Cell Reports,* 6:345–347 (1987) indicates somatic embryogenesis from the tissue cultures of corn leaf segments. Thus, it is clear from the literature that the state of the art is such that these methods of obtaining plants are, and were, "conventional" in the sense that they are routinely used and have a very high rate of success.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottesville, Va. 367–372, (1982)) and in Duncan et al., "The Production of Callus Capable of Plant Regeneration from Immature Embryos of Numerous *Zea Mays* Genotypes," 165 *Planta* 322:332 (1985). Thus, another aspect of this invention is to provide cells which upon growth and differentiation produce rice plants having the physiological and morphological characteristics of hybrid rice line RH101.

The utility of hybrid rice line RH101 also extends to crosses with other species. Commonly, suitable species will be of the family Graminaceae, and especially of the genera *Zea, Tripsacum, Croix, Schlerachne, Polytoca, Chionachne,* and *Trilobachne,* of the tribe Maydeae. Potentially suitable for crosses with RH101 may be the various varieties of grain sorghum, *Sorghum bicolor* (L.) Moench.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed hybrid.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Corn Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.,* 210:86 (1987), Svab et al., *Plant Mol. Biol.* 14:197 (1990< Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include -glucuronidase (GUS, -galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

Recently, in vivo methods for visualizing GUS activity that do not require destruction of plant tissue have been made available. Molecular Probes publication 2908, Imagene Green™, p. 1–4 (1993) and Naleway et al.,*J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science*

263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-specific or Tissue-preferred Promoters

A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt-endotoxin gene. Moreover, DNA molecules encoding-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor 1), Sumitani et al., *Biosci. Biotech. Biochem.* 57:1243 (1993) (nucleotide sequence of *Streptomyces nitrosporeus*-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another nonprotein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-1,4-D-polygalacturonases facilitate fungal colonization and plant nutrient release by solubilizing plant cell wall homo- -1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A development-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased Phytate Content
  1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene.
  2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis*-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley-amylase gene), and Fisher et al., *Plant Physiol.* 102:1045 (1993) (maize endosperm starch branching enzyme II).

Methods for Corn Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. *Agrobacterium*-Mediated Transformation

One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 $\mu$m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2–38, p 53 (1990); D'Halluin et al., *Plant Cell* 4:1495–1505 (1992) and Spencer et al., *Plant Mol. Biol.* 24:51–61 (1994).

Following transformation of rice target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular rice line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred rice plant is used in the context of the present invention, this also includes any single gene conversions of that inbred. The term single gene converted plant as used herein refers to those rice plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental rice plants for that inbred. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

DEPOSIT INFORMATION

A deposit of the RiceTec, Inc. proprietary rice hybrid RH101 disclosed above and recited in the appended claims has been made with the American Type Culture Collection (ATCC), 10801 University Blvd., Manassas, Va. 20110. The date of deposit was Oct. 23, 2002. The deposit of 2,500 seeds was taken from the same deposit maintained by RiceTec, Inc. since prior to the filing date of this application. All restriction upon the deposit have been removed, and the deposit is intended to meet all of the requirements of 37 C.F.R.§1.801-1.809. The ATCC accesion No. is PTA-4771. The deposit will be maintained in the depository for a period of 30 years, or 5 years after the last request, or for the effective life of the patent, whichever is longer, and will be replaced during that period.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A rice seed designated RH101, wherein a representative sample of said seed has been deposited under ATCC Accession No. PTA-4771.

2. A rice plant, or a part thereof, produced by growing the seed of claim 1.

3. Pollen of the plant of claim 2.

4. An ovule of the plant of claim 2.

5. A rice plant, or a part thereof, having all of the physiological and morphological characteristics of the rice plant of claim 2.

6. A tissue culture of regenerable cells or protoplasts produced from the rice plant of claim 2.

7. The tissue culture of claim 6 wherein the cells or protoplasts of the tissue culture are produced from a tissue selected from the group consisting of embryos, meristematic cells, pollen, leaves, anthers, roots, root tips, flowers, seeds, and stems.

8. A rice plant regenerated from the tissue culture of claim 7, wherein said plant has all the physiological and morphological characteristics of the rice plant grown from rice seed designated RH101.

9. A method for producing a rice seed comprising crossing a first parent rice plant with a second parent rice plant and harvesting the resultant hybrid rice seed, wherein said first parent rice plant or second parent rice plant is the rice plant of claim 2.

* * * * *